United States Patent [19]

Tateosian et al.

[11] 4,425,094

[45] Jan. 10, 1984

[54] METHOD OF ROOT CANAL THERAPY

[75] Inventors: Louis H. Tateosian, York; James R. Royer, Mount Joy; George T. Eden, York, all of Pa.

[73] Assignee: Dentsply Research & Development Corporation, Milford, Del.

[21] Appl. No.: 261,785

[22] Filed: May 8, 1981

[51] Int. Cl.³ .............................................. A61K 5/01
[52] U.S. Cl. ................................................... 433/228
[58] Field of Search ................. 433/224, 81, 228, 226

[56] References Cited

U.S. PATENT DOCUMENTS

| | | | |
|---|---|---|---|
| Re. 27,401 | 6/1972 | Wichterle et al. | 260/2.5 R |
| 1,649,508 | 11/1927 | Carmichael | 433/224 |
| 2,644,232 | 7/1953 | Roubian | 433/228 |
| 3,082,526 | 3/1963 | Nitzsche et al. | 433/224 |
| 3,792,028 | 2/1974 | Seiderman | 260/80.72 |
| 3,822,238 | 7/1974 | Blair et al. | 260/75 NK |
| 3,868,447 | 2/1975 | Kliment | 424/81 |
| 3,874,082 | 4/1975 | Stein | 433/228 |
| 3,925,895 | 12/1975 | Kliment et al. | 433/224 |
| 3,929,741 | 12/1975 | Laskey | 260/79.3 M |
| 3,975,350 | 8/1976 | Hudgin et al. | 260/30.4 N |
| 4,156,066 | 5/1979 | Gould | 528/73 |
| 4,156,067 | 5/1979 | Gould | 528/73 |
| 4,181,983 | 1/1980 | Kulkarni | 3/1 |
| 4,192,827 | 3/1980 | Mueller et al. | 525/123 |

FOREIGN PATENT DOCUMENTS 220491 8/1924 United Kingdom ................ 433/224

OTHER PUBLICATIONS

Langeland et al., Biological Evaluation of Hydron, May 1981, J. Endodontics, vol. 7, No. 5, pp. 196–204.
Nguyen, Obturation of the Root Canal System, Pathways of the Pulp, 2nd Ed., Chapter 8, pp. 133–195.

*Primary Examiner*—John J. Wilson
*Attorney, Agent, or Firm*—Woodcock, Washburn, Kurtz, Mackiewicz & Norris

[57] ABSTRACT

Endodontic filling systems are provided having improved properties over those known to the prior art. Endodontic points are provided comprising hydrophilic, polymeric compositions. Such points are swellable when placed into a prepared root canal space and provide substantially complete filling of lateral cavity spaces without invasion of the subapicial space. According to a preferred embodiment, such points are used in conjunction with pastes or fluids comprising hydrophilic, polymeric compositions.

23 Claims, 5 Drawing Figures

METHOD OF ROOT CANAL THERAPY

BACKGROUND OF THE INVENTION

1. Field of the Invention

This invention is concerned with endodontic filling systems having improved properties over those known to the prior art. More particularly, this invention deals with materials which are useful in endodontic dentistry, especially in root canal filling applications, and with methods and procedures employing such materials for endodontic therapy.

Endodontics or root canal therapy is that branch of dentistry which deals with the diseases of the dental pulp and associated tissues. One aspect of endodontics comprises the treatment of infected root canals, the removal of diseased pulp tissues, followed by the biomechanical modification and the subsequent filling of the pulp canal (root canal). FIG. 1 is a representation of tooth anatomy insofar as it is relevant to an understanding of the present invention.

Those skilled in the art will recognize that root canal therapy is generally indicated for teeth having sound external structures but having diseased, dead or dying pulp tissues. Accordingly, such teeth will generally possess intact enamel 10 and dentin 12, and be satisfactorily engaged with the bony tissue 20, by, inter alia, healthy periodontal ligaments 18. In such teeth, the pulp tissue 14, and excised portions of the root 16, should be replaced by a biocompatible substitute. notice should be taken of the apical foramen 22, the orifice through which blood and nerves pass to support the pulp tissues.

One technique known to those skilled in the art for the preparation of a root canal for filling is represented by figures 2a-2e. A tooth having a basically sound outer structure 24 but diseased pump 26, is cut with conventional dental drill means 28 creating a coronal access opening 30. A broach is used for gross removal of pulp material 26 from the root canal through the coronal access opening 30. The void thus formed is enlarged as in FIG. 2d with reamers and/or files 34, to result in a fully excavated cavity 36. Debris is removed from this cavity by flushing and the cavity cleansed to remove all diseased tissue. Following chemical antisepsis, the escavated canal is ready for filling.

As may be seen in FIG. 3, the prepared canal 36 is not smooth; it comprises numerous lateral spaces such as fissures, accessory canals and cut tubules 38. Some of these irregular structures result from natural morphology while others are artifacts of cavity preparation. It should also be noted that the removal of the pulp tissues effects the removal of the contents of the pump chamber and root canal nearly to the root apex. In practice, however, the apical foramen 22 is occasionally enlarged and some limited subapical space is affected by the preparation.

The filling of prepared root canals has traditionally been accomplished through the use of solid, shaped filling bodies or "points." thus, tapered cones or "points" of silver or gutta percha of the correct size for the canal to be filled are selected, coated with a cement, and placed in the prepared canal. In the case of silver and occasionally gutta percha, a single point may be placed in an attempt to fill the root canal completely. Multiple points of gutta percha may be wedged into a canal to advance the same end. The employment of either silver or gutta percha does not generally result in complete filling of the lateral spaces of the prepared canal. The presence of voids in the filled canal space is believed to foster the growth of bacteria; such incomplete filling is to be avoided. At the same time, it is desirable to control carefully the insertion of root canal filling material and cement to avoid overfilling. Excessive tamping or instrumentation of gutta percha points tends to cause extrusion of the cement used therewith and sometimes the points themselves through the apical foramen into the subapical space. Incorrect placement of a silver point and cement can result in a similar problem. Such extrusion is generally believed to be harmful, to cause irritation of the tissues located at the apex, and to retard the healing thereof.

One attempt to improve the filling efficiency of root canal filling media has employed polymerizable, hydrophilic fluids or pastes. Such fluids or pastes are injected into the prepared root cavity, invading and filling many of the irregularities 38 in the canal. They are then polymerized in situ. While such materials and processes employing them properly address the need for lateral space filling during root canal therapy, certain significant shortcomings are associated therewith. A principle shortcoming in the employment of such polymerizable paste filling formulations in root canal therapy is the tendency of such materials to overfill the cavity. Because of the fluid nature of such pastes, it has been found that significant portions thereof may be extruded through the apical foramen into the subapical space. Additionally, polymerization of such pastes is initially accompanied by a small but significant amount of shrinkage. This shrinkage, approximately 3% of the initial volume, may facilitate the transport of infectious agents and threaten the filled root canal with further microbial attack. The employment of such pastes may also result in the establishment of voids within the filling structure leading to structural inhomogeneity. Swelling then follows polymerization and the initial shrinking, which swelling can result in a net gain in volume of about 8-9% of the initial volume. A further disadvantage is the probable extraction of residual unreacted monomer, plasticizer, accelerator and initiator into the aqueous body fluids.

Further disadvantages also attend the use of such paste filling systems. The employment of endodontic filling pastes presently requires a complex and technically difficult mixing, dispensing, and instrument cleaning routine for use. Thus, the use of such materials requires the mastery of a new therapeutic technique by the endodontic dentist and leads to the likelihood of process errors thereby.

A thorough overview of the State of the Art in endodontic filling materials and processes is presented in "Obturation of the Root Canal System" in *Pathways of the Pulp*, Cohen et al eds., C.V. Mosby (1980) which is incorporated herein by reference.

DESCRIPTION OF THE PRIOR ART

It is known to employ hydrophilic polymers for the construction of solid, aqueous fluid-swellable bodies for use as prosthetic devices. Thus, various acrylic, pyrrolidone and other species have been used for the construction of soft contact lenses, soft tissue implants, intrauterine devices, pessaries, and the like. See, for example, U.S. Pat. Nos. RE 27,401 reissued June 20, 1972 to Wichterle et al and 3,792,028 issued Feb. 2, 1974 to Seiderman. It has not been suggested to employ such hydrophilic, swellable bodies in endodontic dentistry.

U.S. Pat. No. 4,181,983 issued Jan. 8, 1980 to Kulkarni is drawn to assimilable hydrophilic prostheses useful in medical and dental repair. Thus, polymeric prolactic acids are used for implantable devices. These polymers are assimilated slowly by the body allowing gradual healing of abscesses, sockets, and the like. the polymerized prolactic acid is modified to make the polymer hydrophilic.

U.S. Pat. No. 3,929,741 was issued Dec. 30, 1975 to Laskey for hydrophilic acrylamido polymers. While this reference is drawn primarily to sulfinamido species, columns 2-4 discuss hydrophilic polymers generally. These materials are said to be suitable for body implants, contact lenses, burn dressings and other biological applications including certain dental uses.

U.S. Pat. No. 3,925,895 issued Dec. 16, 1975 to Kliment et al for hydrophilic root canal filling material. This reference is directed to endodontic dentistry employing liquid or paste polymerizable compositions. Numerous materials are suitable for use in this system including a wide variety of acrylic species.

U.S. Pat. No. 3,868,447 issued Feb. 25, 1975 to Kliment for HEMA paste. A hydrophilic paste comprising an organic solvent-soluble hydrophilic copolymer of a hydroxy lower alkenyl acrylate or methacrylate and a minor proportion of the diester of a glycol and acrylic acid or methacrylic acid together with fillers and an organic solvent for the copolymer is disclosed. The organic solvent-soluble pastes according to the '447 patent are disclosed as being useful, inter alia, for carrying local anesthetics in dental surgery and as protective layers for filling during setting.

U.S. Pat. No. 3,082,526 was issued Mar. 26, 1963 to Nitzsche et al for a method and material of filling dental roots. Silicone rubbers are disclosed which are useful for filling caries, root canals and for the taking of dental impressions. Mixtures are thus disclosed of siloxanes and silanes together with optional fillers etc. which are useful in dentistry. The siloxane-silane mixture cures in the presence of water and must be stored in containers from which water is excluded. It is believed that a crosslinking reaction takes place during the curing process.

None of the foregoing is believed to anticipate or to render obvious the subject matter of the present invention.

OBJECTS OF THE INVENTION

It is an object of this invention to provide novel endodontic filling materials and processes which enjoy the benefits of employing hydrophilic filling media without suffering the detriments exhibited by the use of hydrophilic paste formulations. More particularly, it is desired to afford prepolymerized hydrophilic filling bodies or points suitable for use in endodontics. Another object is to provide new root canal filling procedures employing such polymerized hydrophilic bodies. It is also desired to develop new root canal filling techniques which avoid overfilling of the prepared canal into the subapical space. A further object is to provide filling bodies which can effect a seal of the apical foramen and reduce the amount of filling material transported into the subapical space during endodontic filling.

A further object is to identify polymeric hydrophilic materials suitable for use in such endodontic practices which do not shrink upon use and which are swellable so as to facilitate filling of lateral endodontic spaces. An additional object is to provide such materials which are capable of delivering therapeutic agents to endodontic locations both during and after an endodontic procedure so as to provide increased effectiveness of such therapy. These and other objects are obtained through the practice of one or more of the embodiments of the present invention.

DESCRIPTION OF THE DRAWINGS

FIG. 3 shows a prepared tooth canal, FIG. 4 indicates a hydrophilic shaped body in place in the canal and FIG. 5 shows the swollen body filling a portion of the canal.

SUMMARY OF THE INVENTION

Figure 1:
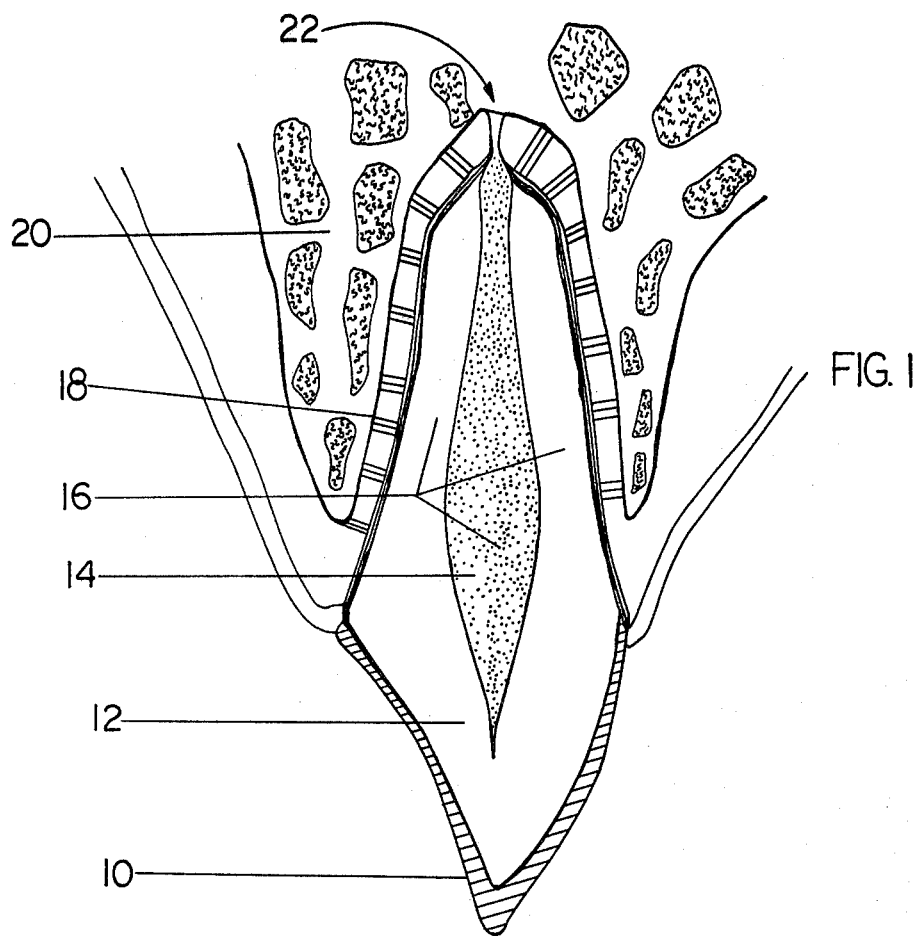
FIG. 1 depicts a mammalian tooth in cross section.
Figure 2:
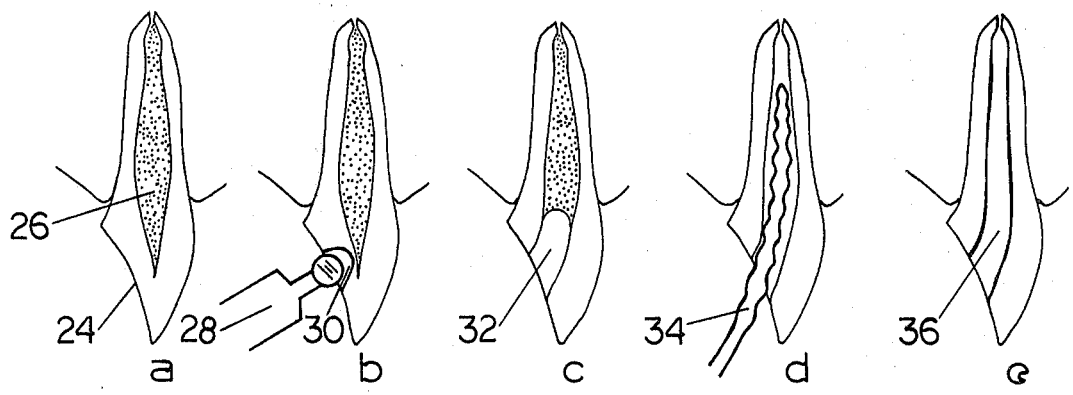
FIGS. 2a-2e represent the procedure employed for preparing a tooth for endodontic restoration.

The objects of this invention are attained through the provision of endodontic points comprising hydrophilic polymeric compositions. More particularly, such endodontic points are provided which are swellable when placed into a prepared root canal space or cavity. The objects are further attained through the employment of endodontic filling processes comprising the steps of removing a substantial portion of the pulp tissue of a tooth being in need of root canal therapy to form a space and placing into said space an endodontic filling system comprising a shaped body comprising a hydrophilic, polymeric composition. It is preferred that such filling system further comprise a hydrophilic, polymeric fluid or paste in conjunction with such hydrophilic, polymeric shaped body or endodontic point.

DETAILED DESCRIPTION OF THE INVENTION

The endodontic filling methods of the present invention employ filling systems comprising shaped bodies of hydrophilic, polymeric compositions. According to a preferred embodiment hereof, such filling systems also employ polymeric, hydrophilic fluids or pastes in conjunction with the shaped bodies. It has been found that when such shaped bodies are inserted into prepared root canals and allowed to swell through absorption of aqueous media, a substantially complete filling of the canal space is accomplished. Such swelling also accomplishes the substantial filling of naturally and artificially created lateral spaces thus to promote the benefits resulting from such substantially complete filling. This filling of lateral spaces is further promoted by employing in conjunction with the hydrophilic shaped bodies of this invention, hydrophilic, polymeric fluids or pastes. Such fluids or pastes may be formulated so as to be capable of injection into the lateral spaces of a prepared root canal through the hydraulic compression thereof by an expanding hydrophilic shaped body or point.

At the same time, use of hydrophilic, polymeric bodies according to the practice of this invention avoids the disadvantages attendant to the use of polymerizable hydrophilic paste type endodontic filling materials alone. Thus, since the shaped bodies are formed from polymerized materials, no postpolymerization shrinkage of polymeric materials occurs interior to the tooth structure to be filled. A further benefit of employing polymerized filling bodies relates to the predictability of swelling of such bodies as compared to pastes. Thus, a cone or point of hydrophilic polymer will swell at a predictable rate and to a predictable increased volume when inserted into a root canal; localized inhomogeneity of swelling is avoided. Accordingly, such shaped polymeric bodies are not likely to cause physical stressing of tooth structure upon filling. Such shaped polymers also do not result in interior voids as polymerizable pastes may do during shrinkage.

Additionally, it has been found that the use of shaped bodies or points of polymerized, hydrophilic compositions largely avoids the injection of endodontic filling material into the subapical space of a tooth via the apical foramen. Accordingly, it is believed that the shaped body or point may be placed in such a fashion so as to seal off the apical foramen and thus prohibit the transmission of filling material therethrough.

The shaped bodies of hydrophilic, polymeric material useful in the practice of one or more embodiments of the present invention may employ a wide variety of polymeric compositions. Thus, the materials of U.S. Pat. No. RE 27,401 Wichterie et al and U.S. Pat. No. 3,792,028 Seiderman, both of which patents have been referred to above may be employed. Numerous other hydrophilic materials such as those disclosed in U.S. Pat. No. 4,192,827 issued to Mueller et al are also useful. The foregoing Wichterle, Seiderman and Mueller patents are incorporated herein by reference to provide illustrative disclosure of the design and formulation of hydrophilic, polymeric materials which may be useful in the practice of this invention. Of those polymeric, hydrophilic materials which are known to those skilled in the art, those disclosed in U.S. Pat. Nos. 3,822,238 issued to Blair et al, 3,975,350 issued to Hudgin et al, 4,156,066 issued to Gould, and 4,156,067 issued to Gould, all of which are believed to be assigned to Tyndale Plains-Hunter Ltd. of Princeton, N.J. are most preferred for the practice of the present invention. Each of the foregoing Tyndale Plains-Hunter patents is incorporated herein by reference to provide those skilled in the art with illustrative descriptions of preferred polymers for use in the practice of the present invention.

It has been found to be preferred to employ as the hydrophilic, polymeric species useful in the formulation of the shaped bodies of the present invention, polyurethanes. More particularly, it is preferred to employ polyurethanes comprising the reaction product of one or more diols, a polyfunctional lactone and an organic polyisocyanate. Such formulations are disclosed, for example, in U.S. Pat. No. 4,156,067 issued to Gould which has been incorporated herein by reference. The material which is presently believed to be best suited for the practice of the present invention is disclosed in example 24 of U.S. Pat. No. 4,156,067 and comprises polyurethanes prepared from the reaction of ethylene glycols, with delta gluconolactone and polyisocyanates.

It is to be understood that other hydrophilic, polymeric systems including the hydroxylic acrylates of Wichterle, the pyrrolidones of Seiderman, the acrylamides of Mueller, and other systems may also be employed in the practice of one or more embodiments of the present invention.

While, a priori, any hydrophilic, polymeric system may be useful in the practice of the present invention, certain physical constraints exist which serve to limit those which are preferred. Accordingly, those skilled in the art will appreciate that in order to provide shaped bodies of hydrophilic, polymeric materials, it is necessary that such materials be shape retaining. Accordingly, substantial stiffness or "body" must be present in such compositions. Those skilled in the art will readily be able to formulate numerous types of hydrophilic polymers which are capable of retaining a shape, especially a conical shape or endodontic point. It is elementary that the thickness, "body," or viscosity of such polymeric systems may be modified by the employment of certain filling materials. Accordingly, certain organic and/or inorganic fillers may be included therein. It is also desired that the endodontic point be substantially opaque to X-radiation so as to facilitate the location and identification of such point by dental professionals. Accordingly, the inclusions of radiopaque fillers such as barium glass or barium sulfate is preferred.

The shaped bodies of the present invention may be formulated to comprise antibiotic, cariostatic, antibacterial, or other antiinflammatory, biologically active or therapeutic materials. The therapeutic compositions may be included in the hydrophilic, polymers of the shaped endodontic bodies to transport such agents to the tooth interior. Continuing antisepsis of the filled root canal may, for example, be accomplished thereby. The therapeutic agents may be included in therapeutically effective amounts.

As has been indicated previously, it is preferred to employ conjointly with the shaped bodies of the present invention hydrophilic, polymeric fluids or pastes. As has been suggested, such fluids or pastes facilitate the substantially complete filling of lateral fissures or voids in prepared root canals. In general, the fluids or pastes may be prepared from any of the hydrophilic, polymeric materials which are useful in the formulation of the hydrophilic shaped bodies of the present invention. It is preferred, however, that they have a lesser viscosity or thickness when compared with the shaped bodies so as to be more readily able to penetrate such lateral spaces. Those compositions disclosed in example 24 of U.S. Pat. No. 4,156,067, which has been incorporated herein by reference, are also most preferred for the preparation of such hydrophilic fluids or pastes. Inclusion of certain viscosity reducing agents such as ethyl alcohol, water, or other biologically acceptable fluids, is preferably employed, however.

Such fluids or pastes may be employed in conjunction with endodontic points such as gutta percha, silver, etc. to result in good filling of canal spaces. Indeed, such pastes may also be used alone to fill root canals. Since these hydrophilic pastes or fluids are polymerized, shrinkage due to polymerization is avoided.

Figure 3:
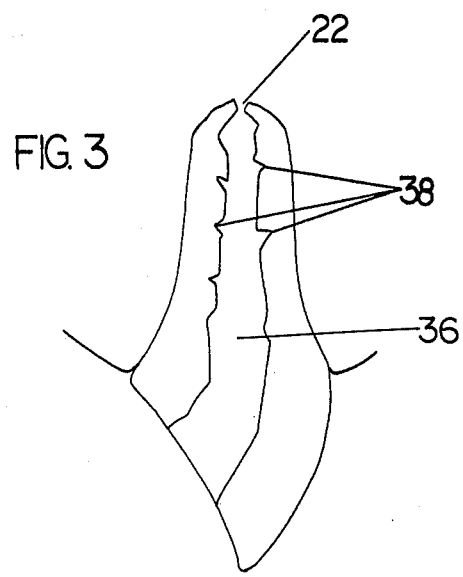
FIGS. 3-5 depict sequential steps in the present process for endodontic filling. Thus.
Figure 4:
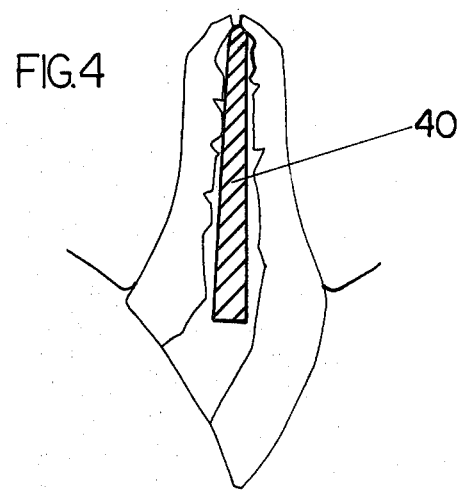
Figure 5:
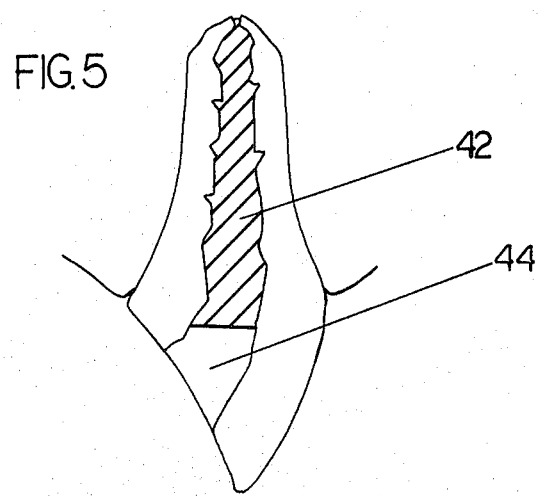

The mode of action of the endodontic filling system according to the present invention may be more fully understood by reference to FIGS. 3-5. Accordingly, a shaped body comprising a hydrophilic, polymeric composition 40, is inserted into a prepared root canal 36. The hydrophilic body, which preferably is in the shape of an endodontic point, is so selected and situated as to fit snugly within the interior portion of the prepared canal. Preferably, the tip of the shaped body is located adjacent to the apical foramen and, even more preferably, is selected and positioned so as to plug or fill that orifice. The hydrophilic shaped body then absorbs aqueous fluid either via the tooth or otherwise and swells, thus substantially filling the lateral spaces, fissures and voids 38, generally found in prepared root canals. It is believed that the shaped body does not substantially swell past the apical foramen into the subapical space and that, accordingly, minimal invasion thereof occurs.

According to a preferred embodiment, the shaped body or endodontic point is used in conjunction with a hydrophilic, polymeric fluid or paste. In such a fashion, the point may be coated with such paste prior to its insertion into the prepared root canal. Alternatively, an amount of paste may be placed into the canal prior to the insertion of the shaped body. In either event, it is believed that in most cases, effective sealing of the apical foramen by the shaped body occurs thus to preclude substantial invasion of the subapical space by the fluid or paste.

It is frequently desired to finish the filling of a prepared root canal using the present invention with materials other than hydrophilic, polymeric compositions. Accordingly, a minor proportion of the prepared canal 44 may be allowed to remain in the prepared canal after a major proportion of the canal has been filled with the hydrophilic, polymeric system of the present invention. This space is preferably filled with a hardenable composition such as those which are well known to those skilled in the art. Accordingly, the space 44 may be filled with amalgam, polymeric composite restorative, or other filling composition thus to "face" the cavity.

The following examples are included for purposes of illustration only and are not to be construed as limiting the scope of the invention which is defined more particularly in the claims.

EXAMPLE 1

A hydrophilic, polymeric urethane was formulated from the following constituents:

| polyethylene glycol | 54.6 g |
| diethylene glycol | 8.7 g |
| delta gluconolactone | 5.8 g |
| methylene bis(4-cyclohexyl isocyanate) (Desmodur W-Mobay) | 40.4 g |
| dibutyl tin dilaurate | 0.04 g |
| | 109.54 g |

The polyethylene glycol and diethylene glycol are melted together at 70° C. and the delta gluconolactone and Desmodur W are added with stirring until homogeneity is achieved. The mixture is cooled to 45° C. and the dibutyl tin dilaurate is added rapidly with stirring. Stirring is continued for about 15 minutes during which time the exothermic heat of reaction causes the temperature to rise to about 85° C. with a resulting increase in viscosity. The polymer is poured while still viscous into a pan which is placed in an oven at 75° C. for 20 minutes. The pan is then removed from the oven and cooled at room temperature. The resulting polymer was used immediately to formulate endodontic points or other shaped bodies by cutting, slitting, rolling or otherwise shaping the polymeric mass.

EXAMPLE 2

A radiopaque shaped body or endodontic point was formed as follows. A hydrophilic polymeric urethane similar to the polymer of Example 1, was formulated except that 50% by weight of barium sulfate and minor amounts of pigments were added slowly in increments to prevent clumping during the first mixing step at 70° C. The mixture was then cooled to 45° C. and the dibutyl tin dilaurate added. This polymer was extruded at 143° C. into rod stock of a diameter approximating the largest section of a commercial endodontic point. The rod stock was placed in distilled water for 24 hours at a ratio by weight of 1:10 rod stock to water, completely to extract any water-soluble residual materials present in the polymeric rod stock. The extruded rod was then cut to the length of a commercial endodontic point, placed on a heated plate at about 140° C., and manually rolled with a tapered acrylic block into a shaped body having a conical section. The hydrophilic points were rolled by the same method used to fabricate gutta percha points with the exception that preformed rod stock was employed.

EXAMPLE 3

A hydrophilic, polymeric urethane was formulated according to the procedure of Example 1 from the following constituents:

| polyethylene glycol | 54.6 g |
| diethylene glycol | 8.7 g |
| delta gluconolactone | 2.9 g |
| methylene bis(4-cyclohexyl isocyanate) (Desmodur W-Mobay) | 40.4 g |
| dibutyl tin dilaurate | 0.04 g |
| water | 0.21 g |
| | 106.85 g |

The water is added together with the lactone.

EXAMPLE 4

A polymeric, hydrophilic paste was formed by blending 32.0 g of the polymer of Example 3 with 73.3 g of ethyl alcohol (95%), 3.4 g deionized water, 38.0 g barium sulfate and 3 g fumed silica. The polyurethane polymer was first allowed to swell in the ethyl alcohol-water solution. The gelatinous material was then placed in a blender. It was blended for 4 minutes until it became homogenous. Next, barium sulfate was mixed in until dispersion was complete. Finally, with blender turned off, fumed silica was added. A smooth, viscous, white paste was formed by blending for two additional minutes.

EXAMPLE 5

A root canal of an extracted upper central tooth was prepared with reamers and files, cleaned, and dried in the normal fashion. A hydrophilic endodontic point formed according to Example 2 was selected having a size designed to obturate the tooth apex. The point was coated with the hydrophilic endodontic paste of Example 4 and inserted into the canal of the tooth. A sufficient amount of the endodontic point was removed with an instrument (preferably hot) to yield an unfilled tooth portion of approximately 2 mm. This unfilled portion was sealed with Finesse TM filling material (a trademark of the L.D. Caulk Division of Dentsply International Inc.). The *in vitro* tooth was then immersed in saline solution to complete the swelling of the hydrophilic endodontic filling material. Examination of the filled tooth by radiography revealed an apparently completely obturated root canal. Subsequent sectioning of that tooth confirmed complete filling of the prepared root canal by the hydrophilic polymeric materials thus employed.

EXAMPLE 6

A root canal of an extracted upper central tooth with limited canal irregularities was prepared with reamers and files, cleaned, and dried in the normal fashion. A hydrophilic endodontic point formed according to Example 2 was selected having a size designed to obturate the tooth apex. The uncoated point was inserted into the canal of the tooth. A sufficient amount of the endodontic point was removed with a hot instrument to yield an unfilled tooth portion of approximately 2 mm. This unfilled portion was sealed with Finesse ™ filling material (a trademark of the L.D. Caulk Division of Dentsply International Inc.). The *in vitro* tooth was then immersed in saline solution to complete the swelling of the hydrophilic endodontic filling material. Examination of the filled tooth by radiography revealed an apparently completely obturated root canal. Subsequent sectioning of a tooth as prepared herein confirmed complete filling of the prepared root canal by the hydrophilic polymeric material thus employed.

EXAMPLE 7

The polymeric, hydrophilic paste of Example 4 was coated onto a gutta percha point, a silver point, and a hydrophilic point similar to that of Example 2. The three coated points were immersed in water for 20 minutes then removed and examined visually and physically. It was observed that the paste coatings swelled and became solid. The solid coatings surprisingly adhered to the silver point as well as to the gutta percha and urethane points. The coating was indistinguishable from the urethane point. In all cases, the hydrated coating was a tough, rubbery, shape-retaining mass. Such hydrophilic pastes were suitable for use endodontically in conjunction with all three types of points.

What is claimed is:

1. A method of filling a tooth in root canal therapy comprising:
   removing a substantial portion of the pulp tissue of said tooth to form a space,
   placing into said space an endodontic filling system comprising a solid shaped body swellable when placed into said space comprising a hydrophilic polymeric composition, and
   permanently sealing said space.

2. The method of claim 1 wherein said filling system further comprises a hydrophilic, polymeric fluid.

3. The method of claim 2 wheren each of said polymeric composition and said polymeric fluid comprises the reaction product of at least one diol, and an organic polyisocyanate.

4. The method of claim 2 wherein said sealing comprises facing an external portion of said space with a hardenable non-hydrophilic composition.

5. The method of claim 1 wherein said filling system further comprises a hydrophilic, polymeric paste.

6. The method of claim 5 wherein each of said polymeric composition and said polymeric paste comprises the reaction product of at least one diol, and an organic polyisocyanate.

7. The method of claim 5 wherein said sealing comprises facing an external portion of said space with a hardenable non-hydrophilic composition.

8. The method of claim 1 further comprising allowing said shaped body to swell.

9. The method of claim 8 wherein said swelling is sufficient substantially to fill at least a major proportion of said space.

10. The method of claim 8 wherein said sealing comprises facing an external portion of said space with a hardenable non-hydrophilic composition.

11. The method of claim 1, 2, 5 or 8 wherein said body further comprises a therapeutic agent.

12. The method of claim 1 wherein said polymeric composition comprises a polyurethane comprising the reaction product of at least one diol, and an polyisocyanate.

13. The method of claims 12, 3 or 6 wherein said diol is a mixture of polyethylene glycol and diethylene glycol, and said polyisocyanate is methylene bis(4-cyclohexyl isocyanate).

14. The method of claim 1 wherein said sealing comprises facing an external portion of said space with a hardenable non-hydrophilic composition.

15. A method for filling a prepared root canal of a tooth comprising
   placing into said canal a solid endodontic point swellable when placed into said canal comprising a hydrophilic, polymeric composition, and
   permanently sealing said prepared root canal.

16. The method of claim 15 further comprising placing into said canal a hydrophilic, polymeric fluid.

17. The method of claim 15 further comprising placing into said canal a hydrophilic, polymeric paste.

18. The method of claim 15, 16 or 17 wherein said point is allowed to swell after placement.

19. The method of claim 15, 16 or 17 wherein substantially no hydrophilic material is introduced into the subapical space of said tooth.

20. The method of claim 15, 16 or 17 wherein said canal is sealed filled by placing a hardenable non-hydrophilic composition therein.

21. The method of claim 15, 16 or 17 wherein said point further comprises a therapeutic agent.

22. The method of claim 16 or 17 wherein each of said hydrophilic material is the reaction product of at least one diol, and an organic polyisocyanate.

23. The method of claim 15 wherein said polymeric composition is the reaction product of at least one diol, and an organic polyisocyanate.

* * * * *